(12) United States Patent
Yukumoto et al.

(10) Patent No.: US 8,496,806 B2
(45) Date of Patent: Jul. 30, 2013

(54) DEHYDRATOR

(75) Inventors: Atsuhiro Yukumoto, Hiroshima (JP);
Hiroyuki Osora, Hiroshima (JP);
Yoshio Seiki, Hiroshima (JP); Haruaki Hirayama, Mihara (JP); Yukio Tanaka, Hiroshima (JP); Hideo Kashiwagi, Hiroshima (JP); Katsufumi Inoue, Yokohama (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 402 days.

(21) Appl. No.: 12/678,673

(22) PCT Filed: Jan. 13, 2009

(86) PCT No.: PCT/JP2009/050273
§ 371 (c)(1),
(2), (4) Date: Mar. 17, 2010

(87) PCT Pub. No.: WO2009/090929
PCT Pub. Date: Jul. 23, 2009

(65) Prior Publication Data
US 2010/0206789 A1 Aug. 19, 2010

(30) Foreign Application Priority Data
Jan. 18, 2008 (JP) .................. 2008-009092

(51) Int. Cl.
*B01D 19/00* (2006.01)
*B01D 61/10* (2006.01)
*B01D 61/12* (2006.01)
*B01D 1/26* (2006.01)

(52) U.S. Cl.
USPC .............. 210/85; 95/8; 95/46; 95/52; 95/243; 96/9; 96/156; 96/182; 96/218; 210/96.2; 210/180; 210/182; 210/184; 210/188; 210/258; 210/321.72; 210/640; 210/641; 210/770; 210/774

(58) Field of Classification Search
USPC .............. 95/8, 45, 46, 50, 52, 243, 254; 96/6, 96/8, 156, 182, 215, 219, 9; 210/85, 143, 210/182, 184, 188, 321.6, 321.72, 638, 96.2, 210/640, 641, 650, 651, 774, 180, 770
See application file for complete search history.

(56) References Cited

U.S. PATENT DOCUMENTS
3,370,102 A * 2/1968 Clifford et al. ............... 585/818
(Continued)

FOREIGN PATENT DOCUMENTS
DE 3526755 A1 1/1987
(Continued)

OTHER PUBLICATIONS
Supplementary European Search Report dated Mar. 14, 2012, issued in corresponding European Patent Application No. 09702932.6.
(Continued)

*Primary Examiner* — Joseph Drodge
(74) *Attorney, Agent, or Firm* — Westerman, Hattori, Daniels & Adrian, LLP

(57) ABSTRACT

Provided is a dehydrator that requires no excessively large apparatus structure and achieves cost-saving while maintaining suction efficiency at a desired level by use of suction means. A dehydrator 100 for separating water from a target liquid 13 includes at least two water separation membrane units 1a and 1b which are provided in series in a flow direction of the target liquid 13. The water separation membrane unit 1a on an upstream side out of the water separation membrane units 1a and 1b is connected to suction means 7 for sucking a gas phase containing water through one condenser 4, and the one condenser 4 condenses water in the gas phase and thereby separates the water. The gas phase sucked by the suction means 7 from the one condenser 4 is transferred to at least one downstream condenser 8 provided downstream of the one condenser 4, and the downstream condenser 8 condenses water in the gas phase and thereby separates the water. The water separation membrane unit 1b on a downstream side of the water separation membrane unit 1a is connected to a steam ejector 3, and the condenser 4 for condensing water in a gas phase passed through the steam ejector 3 condenses water and thereby separates the water.

5 Claims, 1 Drawing Sheet

U.S. PATENT DOCUMENTS

| | | | |
|---|---|---|---|
| 5,013,447 A * | 5/1991 | Lee et al. | 210/640 |
| 5,071,451 A * | 12/1991 | Wijmans | 95/47 |
| 5,151,190 A | 9/1992 | Seiryo | |
| 5,256,296 A * | 10/1993 | Baker et al. | 210/640 |
| 5,616,247 A * | 4/1997 | Mita et al. | 210/640 |
| 6,273,937 B1 * | 8/2001 | Schucker | 95/45 |
| 8,002,953 B2 * | 8/2011 | Lee et al. | 203/19 |
| 8,128,826 B2 * | 3/2012 | Plante et al. | 210/640 |
| 8,287,735 B2 * | 10/2012 | Hanemaaijer et al. | 210/640 |
| 2007/0031954 A1 * | 2/2007 | Mairal et al. | 435/161 |
| 2009/0246848 A1 * | 10/2009 | Noel | 435/165 |
| 2010/0213125 A1 * | 8/2010 | Fontalvo Alzate et al. | 210/638 |

FOREIGN PATENT DOCUMENTS

| | | |
|---|---|---|
| JP | 58-21629 A | 2/1983 |
| JP | 58-95523 A | 6/1983 |
| JP | 63-162002 A | 7/1988 |
| JP | 1-155928 A | 6/1989 |
| JP | 4-22423 A | 1/1992 |
| JP | 5-31333 A | 2/1993 |
| JP | 7-232026 A | 9/1995 |
| JP | 9-103654 A | 4/1997 |
| JP | 10-113531 A | 5/1998 |
| JP | 2005-161187 A | 6/2005 |

OTHER PUBLICATIONS

International Search Report of PCT/JP2009/050273, mailing date of Apr. 14, 2009.

Japanese Office Action issued May 24, 2013, issued in corresponding Japanese Application No. 2008-00902 (with partial English Translation).

* cited by examiner

DEHYDRATOR

TECHNICAL FIELD

The present invention relates to a dehydrator using a water separation membrane. The dehydrator according to the present invention is suitable for separation of water from organic aqueous solution. More specifically, the present invention relates to a dehydrator for dehydrating a mixture (a target liquid) of water with one of ethanol and propanol, each of which forms an azeotropic composition with water.

BACKGROUND ART

Ethanol has attracted attention as a fuel source alternative to petroleum fuels. The market scale of ethanol is estimated to be 55 million kiloliters for 2010. However, for adopting ethanol as a fuel, it is necessary to purify, by distillation, a crude product obtained from a biomass such as corn, and then to perform dehydration until at least 99.5 wt % is reached.

Conventionally, for the dehydration, an ethanol aqueous solution is concentrated by distillation in a distillation tower until the azeotropic point of the ethanol/water system is nearly reached. Then, dehydration is performed.

In this respect, the present inventors have diligently been developing a dehydration method to which a water separation membrane is applied, as a dehydration method for such an ethanol aqueous solution which is at or close to the azeotropic point. Specifically, in a dehydration method which the present inventors have been developing, a water separation membrane unit is constructed using a water separation membrane, a target liquid such as an ethanol aqueous solution is caused to flow in the water separation membrane unit, and water is sucked through the water separation membrane. Incidentally, a dehydration method according to Patent Literature 1 has been known as a dehydration method which employs a water separation membrane.

However, when the target liquid is caused to flow in the water separation membrane unit, water vaporizes, which is accompanied by removal of latent heat. This causes a tendency that the temperature of the target liquid becomes lower in the flow direction. The temperature decrease has resulted in a drawback that the partial pressure of water is lowered, which in turn makes it impossible to maintain a sufficient driving force for the suction and thus disables suction means from exhibiting the function thereof.

Accordingly, there have been demands to solve such a drawback to prevent the temperature decrease and to maintain the driving force, and also a demand to require no excessively large equipment.

[Patent Literature 1] Japanese Patent Application Publication No. Sho 58-21629

DISCLOSURE OF THE INVENTION

Problems to be Solved by the Invention

The present invention has been made in consideration of the above-described circumstances, and an object of the present invention is to provide a dehydrator that requires no excessively large apparatus structure and achieves cost-saving while maintaining suction efficiency at a desired level by use of suction means.

Means for Solving the Problems

To achieve the above object, a dehydrator according to the present invention is a dehydrator for separating water from a target liquid including at least two water separation membrane units which are provided in series in a flow direction of the target liquid. A water separation membrane unit on an upstream side out of the water separation membrane units is connected to suction means for sucking a gas phase containing water through one condenser, and the one condenser condenses water in the gas phase and thereby separates the water. The gas phase sucked by the suction means from the one condenser is transferred to at least one downstream condenser provided downstream of the one condenser, and the downstream condenser condenses water in the gas phase and thereby separates the water. A water separation membrane unit on a downstream side of the water separation membrane unit is connected to a steam ejector, and a condenser for condensing water in a gas phase passed through the steam ejector condenses water and thereby separates the water.

The dehydrator according to a preferred embodiment of the present invention includes: a concentration meter for measuring a concentration of the target liquid on a real time basis at an outlet of the water separation membrane unit on the upstream side; and a membrane outlet concentration controller for controlling suction performance of the suction means on the basis of a value of the concentration detected by the concentration meter.

The dehydrator according to a preferred embodiment of the present invention includes: a concentration meter for measuring a concentration of the target liquid on a real time basis at an outlet of the water separation membrane unit on the downstream side; and a membrane outlet concentration controller for controlling an amount of steam of the steam ejector on the basis of a value of the concentration detected by the concentration meter.

In the dehydrator according to a preferred embodiment of the present invention, the target liquid is an ethanol aqueous solution.

In the dehydrator according to a preferred embodiment of the present invention, a gas phase passed through the water separation membrane units on the upstream side is merged, at the one condenser, with a gas phase sucked through the water separation membrane unit on the downstream side by motive steam of the steam ejector and the motive steam, and water in a gas phase obtained by the merger is condensed and thereby is separated.

Regarding the above-described target liquid, the dehydrator of the present invention can generally be applied to organic aqueous solutions, if conditions permit. An organic component in the organic aqueous solution is preferably one organic component selected from the group consisting of: alcohols such as ethanol, propanol, isopropanol, and glycols; carboxylic acids such as acetic acid; ethers such as dimethyl ether and diethyl ether; aldehydes such as acetaldehyde; ketones such as acetone and methyl ethyl ketone; and esters such as ethyl acetate.

However, a preferable target to which the present invention is applied is a dehydrator whose target liquid is a mixture of water with one of ethanol and propanol, each of which forms an azeotropic composition with water.

Effects of the Invention

According to the present invention, provided is a dehydrator a dehydrator that requires no excessively large apparatus structure and achieves cost-saving while maintaining suction efficiency at a desired level by use of suction means.

Specifically, with the dehydrator according to the present invention, for a water separation membrane unit on an upstream side where a partial pressure of water on a primary side is high, the partial pressure of water on a secondary side is set high, thereby allowing the capacity of a vacuum system (suction means) on the secondary side to be reduced. Meanwhile, because of the connection to the suction means for sucking the gas phase containing water through the one condenser, water vapor in the gas phase containing a large amount of water vapor can be separated, by condensation, in the one condenser as water which is mostly in a liquid state, together with a slight amount of ethanol. Thereby, even when the partial pressure of water on the secondary side is set high, the load on the suction means can be reduced.

Moreover, when the gas phase passed through the water separation membrane unit on the upstream side is merged, at the one condenser, with the gas phase sucked through the water separation membrane unit on a downstream side by motive steam of a steam ejector and the motive steam, a motive water vapor of the steam ejector is mixed, in the first condenser, with a processed fluid passed through the water separation membrane unit on the downstream side. Thereby, the alcohol concentration is lowered, and the ethanol concentration on the gas phase side is lowered because of vapor-liquid equilibrium. For this reason; the amount of alcohol entering the suction means can be reduced.

Furthermore, it is possible to appropriately maintain the operation conditions of the apparatus, with the configuration where the concentration meter for measuring the concentration at the outlet of the water separation membrane unit on a real time basis is provided, and where the membrane outlet concentration controller is provided for controlling the suction performance of the suction means or for controlling the amount of steam of the steam ejector, on the basis of the value of the concentration detected by the concentration meter.

Figure 1:
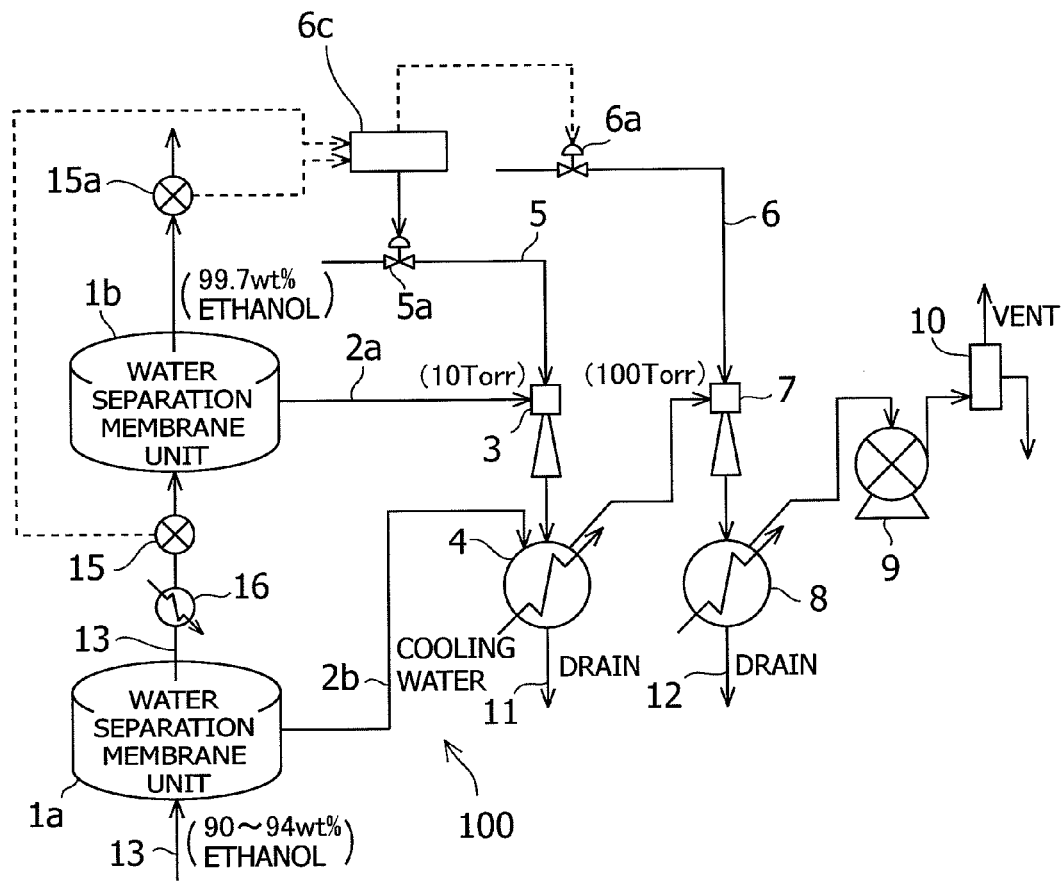
FIG. 1 is a schematic diagram of a dehydrator according to a first embodiment of the present invention.

EXPLANATION OF REFERENCE NUMERALS 1a, 1b Water separation membrane unit
3 Steam ejector
4 First condenser
5 Motive steam pipe
5a Steam valve
6a Steam valve
6 Motive steam pipe
6c Membrane outlet concentration controller
7 Steam ejector
8 Second condenser
9 Vacuum pimp
13 Target liquid
15, 15a Ethanol concentration meter
16 Intermediate heater
100 Dehydrator

BEST MODES FOR CARRYING OUT THE INVENTION

Hereinafter, embodiments of a dehydrator according to the present invention will be described in detail with reference to the drawings.
[First Embodiment]
FIG. 1 is a schematic diagram of a dehydrator according to a first embodiment of the present invention.

The dehydrator according to this embodiment is designed for a case where the target liquid to be dehydrated is an ethanol aqueous solution. As for the concentration of this ethanol aqueous solution, this aqueous solution is assumed to have an ethanol concentration from 90 wt % to 94 wt %. Specifically, the target liquid is an ethanol aqueous solution, which contains ethanol as the organic component. The ethanol concentration of an eventually obtained product fluid, i.e., product ethanol (anhydrous ethanol) is 99 wt % to 99.8 wt %.

Water separation membrane units 1a and 1b of a dehydrator 100 according to this embodiment are units for separating an ethanol aqueous solution into anhydrous ethanol and water.

In each of the water separation membrane units 1a and 1b, the target liquid flows on a primary side of a water separation membrane, and permeate water is obtained on a secondary side of the water separation membrane. As will be described later, the water separation membrane is formed in such a manner as to cover an inner tube provided in a porous base member formed in a tubular shape. One or a plurality of such tubular members are housed in a container, and water is separated by suction from the outsides of the tubular members.

A silica-based or zeolite-based inorganic water separation membrane with a pore diameter of 10 angstrom or less is suitable as the water separation membrane for forming each of the water separation membrane units 1a and 1b; alternatively, the water separation membrane may be a carbon membrane.

An inorganic water separation membrane described in Japanese Patent No. 2808479 is also applicable. The inorganic water separation membrane according to Japanese Patent No. 2808479 is an acid-resistant composite separation membrane obtained by supporting, in pores of a porous inorganic material, silica gel obtained through hydrolysis of an ethoxy or methoxy group-containing alkoxysilane. The acid-resistant composite separation membrane can be produced by a production method including the following Steps 1 to 11.

Note that, as a porous base member on which the inorganic water separation membrane is supported, a base member of a ceramic such as alumina, silica, zirconia, or titania is usually used, and a preferable base member is a tubular base member having multiple inner tubes which extend in the longitudinal direction and each of which have a circular cross-section. In the following Steps 1 to 11, the inorganic water separation membrane is formed in a way to cover inner walls of such inner tubes. The target liquid flows in the inner tubes, and water permeates through the water separation membrane, to thereby separate water. The separated water is sucked as water vapor by suction means such as a steam ejector or a vacuum pump. Generally, the separated water is sucked as a gas phase containing such water vapor.

Note that, besides the inorganic water separation membrane, an organic membrane such as a polyvinyl alcohol membrane, a polyimide membrane or a polyamide membrane can be used as the water separation membrane.

Step 1: Blending ratios of raw materials for silica sols to be supported in preparation conditions for multiple kinds of silica sols produced by changing the mixing ratio of an alkoxysilane, which is a raw material of silica sols, water, and an acid catalyst are divided into two kinds, namely, for a silica sol 1 and for a silica sol 2.

Step 2: The weight ratio of water to an alkoxysilane for the raw material of the silica sol 1 is set to 0.5 to 2.0, and the weight ratio of an acid catalyst, which is a reaction catalyst, to the alkoxysilane is set to 0.01 to 0.1.

Step 3: The weight ratio of water to an alkoxysilane for the raw material of the silica sol 2 is set to 2.0 to 50, and the weight ratio of an acid catalyst, which is a reaction catalyst, to the alkoxysilane is set to 0.01 to 0.5.

Step 4: While the above-mentioned raw materials for the silica sol 1 are kept boiling, a liquid approximately 25 minutes after, a liquid approximately 20 minutes after, and a liquid approximately 15 minutes after the start of the boiling are taken as 1-A, 1-B and 1-C liquids, respectively.

Step 5: The above-mentioned raw materials for the silica gel 2 are stirred and mixed at room temperature for 30 minutes to 90 minutes, to produce the silica sol 2.

Step 6: The silica sol 1-A liquid is supported on a surface of a porous base member. Then, the porous base member is baked for 5 to 15 minutes in an electric furnace set at approximately 200° C. Next, the porous base member is baked for 5 to 15 minutes in an electric furnace set at approximately 300° C. Subsequently, the porous base member is baked for 5 to 15 minutes in an electric furnace set at approximately 400° C. Thereafter, the porous base member is baked for 5 to 15 minutes in an electric furnace set at approximately 500° C.

Step 7: The silica sol 1-A liquid is further supported on the surface of the porous base member on which the silica sol 1-A liquid has been supported. Thereafter, the operation in Step 6 is repeated two to three times.

Step 8: Next, by using the silica sol 1-B liquid, similar treatment as in Step 6 and Step 7 is further performed on the surface of the porous base member on which the silica sol 1-A liquid has been supported.

Step 9: Next, by using the silica sol 1-C liquid, similar treatment as in Step 6 and Step 7 is performed on the surface of the porous base member on which the silica sol 1-B liquid has been supported.

Step 10: Next, the silica sol 2 liquid is supported on the surface of the porous base member on which the silica sol 1-A, 1-B and 1-C liquids have been supported. Then, the porous base member is baked for 5 to 15 minutes in an electric furnace set at approximately 200° C. Next, the porous member is baked for 5 to 15 minutes in an electric furnace set at approximately 300° C. Subsequently, the porous base member is baked for 5 to 15 minutes in an electric furnace set at approximately 400° C. Thereafter, the porous base member is baked for 5 to 15 minutes in an electric furnace set at approximately 500° C.

Step 11: The silica sol 2 liquid is further supported on the surface of the porous base member on which the silica sol 2 liquid has been supported. Thereafter, the operation in Step 10 is repeated two to three times.

Via Steps 1 to 11 described above, it is possible to obtain a tubular porous base member (tubular member) in which inorganic water separation membranes are supported (coated) on inner tubes. In the present invention, for example, such a tubular porous base member with the water separation membranes is used as the water separation membrane housed in each of the water separation membrane units $1a$ and $1b$. In each of the water separation membrane units $1a$ and $1b$, such a water separation membrane (tubular member) is housed in a container whose inside pressure can be reduced.

In FIG. 1, the water separation membrane units $1a$ and $1b$ are provided in series with each other in a flow direction of a target liquid 13 containing ethanol. Note that the water separation membrane units $1a$ and $1b$ may be replaced with three or more water separation membrane units provided in series.

The target liquid 13 is introduced into the water separation membrane unit $1a$, and water is separated in the water separation membrane unit $1a$. Then, the target liquid 13 is introduced into the water separation membrane unit $1b$ located downstream. Also in this water separation membrane unit $1b$, water is separated. An intermediate heater 16 is located between the water separation membrane units $1a$ and $1b$, and raises the temperature of the target liquid 13 whose temperature is decreased in the water separation membrane unit $1a$.

In the water separation membrane unit $1a$ on an upstream side out of the water separation membrane units, the gas phase containing water (water vapor) from the target liquid 13 which is made of an ethanol aqueous solution is sucked through a suction path $2b$, and the water is condensed in a first condenser 4. This suction force is given entirely through the condenser 4 by a steam ejector 7. The suction force of the steam ejector 7 is at a pressure level that enables water contained in the gas phase to be condensed in a condenser using cooling water. For example, the suction force is at a level of 100 Ton.

Meanwhile, a steam ejector 3 using the flow of steam from a motive steam pipe 5 provided with a steam valve $5a$ applies a suction force to the water separation membrane unit $1b$ on a downstream side. The suction force of the steam ejector 3 is, for example, at a level of 10 Torr. With such a pressure level, water contained in the gas phase cannot be condensed in a condenser using cooling water. For this reason, water which is from the target liquid 13 and which permeates through the water separation membrane of the water separation membrane unit $1b$ is sucked entirely as water vapor in the gas phase to the steam ejector 3 side.

Then, the gas phase passed through the steam ejector 3 and the motive steam of the steam ejector 3 enter the first condenser 4, and are merged and mixed, in the first condenser 4, with the gas phase which flows from the water separation membrane unit $1a$ on the upstream side and which contains water vapor.

In other words, at the first condenser 4, the gas phase passed through the water separation membrane unit $1a$ on the upstream side is merged with the gas phase passed through the water separation membrane unit $1b$ on the downstream side and the motive steam of the steam ejector 3. A part of water vapor contained in the gas phase is condensed by cooling water, and flows to a drain 11.

The gas phase is further introduced into the steam ejector 7. The motive force of the steam ejector 7 is given by a flow of steam from a motive steam pipe 6 provided with a steam valve $6a$. In this case, the steam ejector 7 may use a process fluid of the plant (any of a gas and a liquid may be used). This is because, for a degree of vacuum at a 100-Torr level, such a fluid can be used alternatively. Note that the steam ejector 7 can be replaced with different suction means such as a vacuum pump, depending on the operation conditions.

Figure 2:
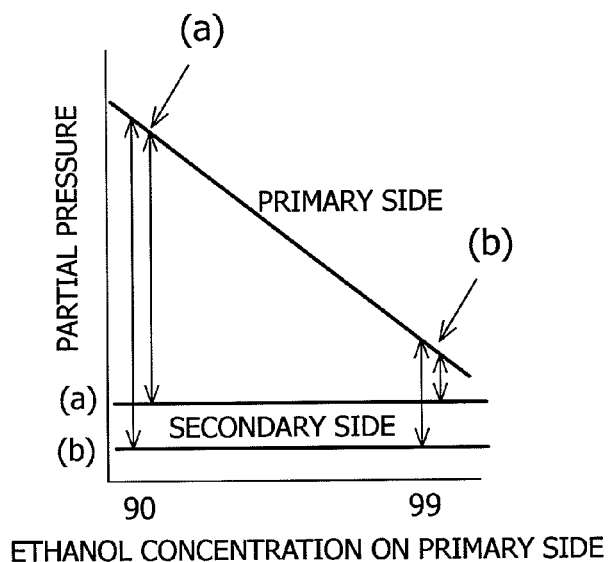
FIG. 2 is a diagram for describing an operation of the present invention.

Incidentally, regarding water in a gas phase, as shown in FIG. 2, when the partial pressure of water on a primary side is high, a difference in partial pressure of water from that on a secondary side is originally great, as in the case of (a), whereas, when a partial pressure of water on the primary side is low, a difference in partial pressure of water from that on the secondary side is small, as in the case of (b).

For this reason, for the water separation membrane unit $1a$ on the upstream side in which a partial pressure of water on the primary side is high, the steam ejector 7 which operates in a state with a relatively low degree of vacuum can be used. In contrast, for the water separation membrane unit $1b$ on the downstream side in which a partial pressure of water on the primary side is low, it is necessary to use a steam ejector which operates at a high degree of vacuum. Note that, in the present invention, the operation is shared as follows: the water separation membrane unit on the upstream side treats a target fluid having an inlet concentration in a range from 90 wt % to 94 wt % (a treatable range is 80 wt % to 96 wt %); and the water separation membrane unit on the downstream side treats a target fluid having a concentration of 97 wt % or higher.

In such a way, the operation is appropriately shared between water separation membrane units on upstream and downstream sides in the dehydrator according to the present invention. Thereby, necessary motive steam for the steam ejectors can be set small.

Meanwhile, in this embodiment, water vapor in a gas phase containing a large amount of water vapor can be separated, by condensation, in the first condenser 4 as water which is mostly in a liquid state, together with a slight amount of ethanol. Thereby, even when a partial pressure of water on the secondary side is set high, the load on the steam ejector 7 (the suction means) can be reduced.

Using a test apparatus, the present inventors compared a case like this embodiment, where a motive force was obtained from the motive steam pipe 5 at 17 kg/h and from the motive steam pipe 6 at 48 kg/h with a case where a suction force of 10 Torr was also obtained from the steam ejector 7, thereby obtaining 120 kg/h of motive steam in total. As a result, in the case like this embodiment, 99.7 wt % product ethanol was successfully obtained. Meanwhile, also in the case of a comparative example where the suction force of 10 Torr was also obtained from the steam ejector 7, 99.7 wt % product ethanol was successfully obtained, and the concentrations of the products of ethanol did not substantially differ from each other. However, much amount of motive steam was required in the comparative example, when compared with this embodiment.

When a 200 thousand t/year-ethanol treatment with an actual apparatus is considered, it is indicated that motive steam of 12 t/h is necessary for a case like the comparative example, whereas, for a case like this embodiment, the amount of necessary motive steam is small like 1.7 t/h from the motive steam pipe 5 and 4.8 t/h from the motive steam pipe 6. Note that, to obtain motive steam of 12 t/h, the steam ejector itself also becomes excessively large.

Moreover, as described above, a processed fluid passed through the water separation membrane unit 1a on the upstream side, a processed fluid passed through the water separation membrane unit 1b on the downstream side, and the motive steam of the steam ejector 3 are mixed with each other in the first condenser 4. Thereby, the ethanol concentration is lowered, and the ethanol concentration on the gas phase side is lowered because of vapor-liquid equilibrium. For this reason, the amount of alcohol entering the steam ejector 7 can be also reduced.

The processed fluid having been subjected to water suction treatment by the steam ejector 7 enters a second condenser 8. In the second condenser 8, water therein is condensed by cooling water, followed by suction by a vacuum pump 9 and emission through a vent 10 to the outside.

In other words, gas phase part in the first condenser 4 and the second condenser 8 is sucked by the suction force of the vacuum pump 9.

Meanwhile, in this embodiment, an ethanol concentration meter 15 for measuring an ethanol concentration on a real time basis is provided at an outlet of the water separation membrane unit 1a, and an ethanol concentration meter 15a for measuring an ethanol concentration on a real time basis is provided at an outlet of the water separation membrane unit 1b. Moreover, signals detected by the ethanol concentration meters 15 and 15a are inputted to a membrane outlet concentration controller 6c.

The ethanol concentration meters 15 and 15a and the membrane outlet concentration controller 6c can be configured into an apparatus capable of measuring an ethanol concentration on a real time basis. In addition, when the target liquid is in its liquid phase, the mass flow rate and the fluid density of the target liquid can be measured with high precision by using a Coriolis flow meter.

In this embodiment, on the basis of the concentration, of the water separation membrane unit 1a on the upstream side, measured by the ethanol concentration meter 15, the membrane outlet concentration controller 6c can optimally control the amount of the steam of the steam ejector 7 corresponding to 100 Torr, by using the valve 6a. Meanwhile, on the basis of the concentration, of the water separation membrane unit 1b on the downstream side, measured by the ethanol concentration meter 15a, the membrane outlet concentration controller 6c can optimally control the amount of the steam of the steam ejector 3 corresponding to 10 Torr, by using the valve 5a.

For example, when the ethanol concentration is lowered, the amount of the motive steam is increased appropriately, thereby making it possible to keep constant the quality of the obtained product. In contrast, if the ethanol concentration is not less than that in a required specification, the amount of the motive steam can be reduced.

Moreover, here, a Coriolis flow meter is provided to each of the outlets, for the target liquid, of the water separation membrane units 1a and 1b, and the amount of the motive steam of each of the steam ejectors 3 and 7 is controlled more appropriately. Thereby, the amount of steam can be optimally controlled in accordance with a target concentration. This is because Coriolis flow meters allow density measurement on a real time basis, and the concentration of the obtained processed fluid can be thus measured on a real time basis, eliminating the delay time in the control.

Hereinabove, the embodiment of the present invention has been described; however, the present invention is not limited to the aforementioned embodiment, and various changes and modifications can be made on the basis of technical ideas of the present invention.

For example, three water separation membrane units can be provided, and three levels of vacuum can be set. In this case, an ejector for sucking water through a second water separation membrane unit on a downstream side can be provided. Then, a gas phase containing water sucked in a first water separation membrane unit on an upstream side can be introduced into a condenser of the ejector for the second water separation membrane unit. Moreover, an ejector for sucking water through a third water separation membrane unit on the most downstream side can be provided. A gas phase containing water sucked in the second water separation membrane unit can be introduced into a condenser of the ejector for the third water separation membrane unit.

Meanwhile, three water separation membrane units can be provided, and two levels of vacuum can be set. In this case, for example, the vacuum levels of the two stages of water separation membrane units (first and second) located upstream can be approximately the same, and the vacuum level on a downstream side can be set high. In this case, an ejector for sucking water through a third water separation membrane unit on the most downstream side can be provided. A gas phase containing water sucked in the first and second water separation membrane units can be introduced into a condenser of the ejector for the third water separation membrane unit. Note that an intermediate heater for supplying heat of vaporization is provided between the first water separation membrane unit and the second water separation membrane unit.

Moreover, four or more water separation membrane units can be provided, and four of more levels of vacuum can be set. Also in this case, as can be understood by those of skill in the art, a vacuum system and a condenser system can be configured in accordance with the above-described concept.

As a further modified embodiment, for example, suppose a case where four or more water separation membrane units are provided and four or more levels of vacuum are set, and where first to fourth water separation membrane units are provided from the upstream to the downstream. In this case, a configuration can be employed in which a vacuum system (an ejector or the like) and a condenser system corresponding thereto are provided for the first water separation membrane unit and the third water separation membrane unit, and a vacuum system (an ejector or the like) and a condenser system corresponding thereto are provided for the second water separation membrane unit and the fourth water separation membrane unit.

As described above, a dehydrator according to the present invention can be configured in accordance with the number of stages of water separation membrane units and the number of stages of levels of vacuum. In short, basically, a gas phase containing water sucked through a water separation membrane unit at a level of vacuum is introduced into a condenser at an outlet of an ejector from a water separation membrane unit on a downstream side. Thus, a dehydrator according to the present invention can be configured, irrespective of the number of the stages.

In consideration of the balance with levels of vacuum and the like, an intermediate heater for supplying latent heat of vaporization of the steam containing water (for example, the intermediate heater 16 in FIG. 1) between water separation membrane units can be provided as appropriate, or the provision of the intermediate heater can be made unnecessary.

The invention claimed is:

1. A dehydrator for separating water from a target liquid, comprising:
   at least two water separation membrane units which are provided in series in a flow direction of the target liquid, wherein
   an upstream water separation membrane unit is connected to suction means for sucking a gas phase passing through the upstream water separation membrane unit and containing water through one condenser, and the one condenser condenses water in the gas phase and thereby separates the water,
   the gas phase sucked by the suction means from the one condenser is transferred to at least one downstream condenser provided downstream of the one condenser, and the downstream condenser condenses water in the gas phase and thereby separates the water, and wherein
   a downstream water separation membrane unit on a downstream side of the upstream water separation membrane unit is connected to a steam ejector, and a condenser for condensing water in a gas phase passing through the steam ejector condenses water and thereby separates the water.

2. The dehydrator according to claim 1, comprising:
   a concentration meter for measuring a concentration of the target liquid on a real time basis at an outlet of the water separation membrane unit on the upstream side; and
   a membrane outlet concentration controller for controlling suction performance of the suction means on the basis of a value of the concentration detected by the concentration meter.

3. The dehydrator according to any one of claim 1, comprising:
   a concentration meter for measuring a concentration of the target liquid on a real time basis at an outlet of the water separation membrane unit on the downstream side; and
   a membrane outlet concentration controller for controlling an amount of steam of the steam ejector on the basis of a value of the concentration detected by the concentration meter.

4. The dehydrator according to any one of claim 1, wherein the target liquid is an ethanol aqueous solution.

5. A dehydrator according to claim 1, wherein
   the gas phase passing through the upstream water separation membrane unit is merged, at the one condenser, with a gas phase sucked through the downstream water separation membrane unit by motive steam of the steam ejector, and the motive steam, and water in a gas phase obtained by the merger is condensed and thereby is separated.

* * * * *